United States Patent [19]
Danet et al.

[11] Patent Number: 5,459,320
[45] Date of Patent: Oct. 17, 1995

[54] TOMOGRAPHY MACHINE WITH GAMMA-RAY DETECTION

[75] Inventors: Bernard Danet, Toulouse; Pierre Gantet, Ramonville Saint Agne; Bernard Aragon, Auzeville; Robert Guiraud, Toulouse, all of France

[73] Assignee: Universite Paul Sabatier, Toulouse Cedex, France

[21] Appl. No.: 364,404

[22] Filed: Dec. 23, 1994

Related U.S. Application Data

[63] Continuation of Ser. No. 920,314, Oct. 23, 1992.

[30] Foreign Application Priority Data

Feb. 23, 1990 [FR] France ................................ 90 02289

[51] Int. Cl.⁶ .................................................. G01T 1/164
[52] U.S. Cl. ...................................... 250/363.04; 378/149
[58] Field of Search ........................... 250/363.1, 363.04, 250/363.06; 378/149

[56] References Cited

U.S. PATENT DOCUMENTS 3,509,341  4/1970  Hindel .
4,831,261  5/1989  Genna et al. ................... 250/363.04

FOREIGN PATENT DOCUMENTS 2471610  12/1979  France .
2351450   6/1975  Germany .
2461877   7/1976  Germany ................................ 378/87
2030422   9/1978  United Kingdom .

OTHER PUBLICATIONS

P. Spiegler, "Approximate Expression for the Geometric Response and the Index of Resolution of Focused Collimators," *Journal of Nuclear Medicine*, vol. 12, No. 8, 1971, pp. 547–551.

*Primary Examiner*—Paul M. Dzierzynski
*Assistant Examiner*—Richard Hanig
*Attorney, Agent, or Firm*—Pollock, Vande Sande & Priddy

[57] ABSTRACT

A tomography machine with gamma ray detection has a collimator, the arrangements of holes of which are focused on a geometric slice of a patient's body, the slice having a thickness determined a priori, for the examination of the slice. Reconstructed tomographic images of this body are obtained swiftly and efficiently. By shifting the tomography machine longitudinally, images of adjacent slices are obtained. This technique makes it possible to work with greater speed than by acquiring comprehensive 2D image projections of the entire body to be studied.

10 Claims, 3 Drawing Sheets

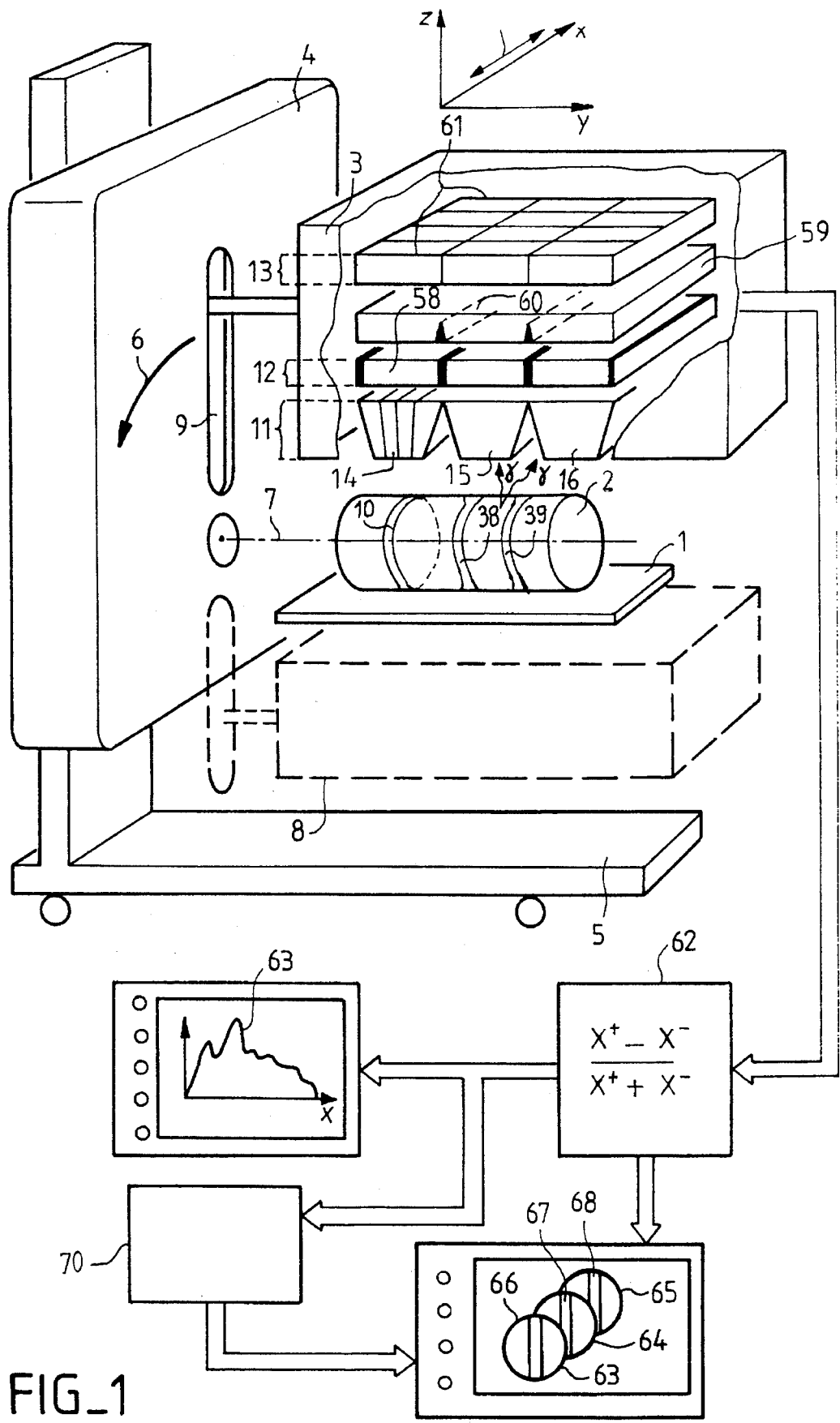
FIG_1

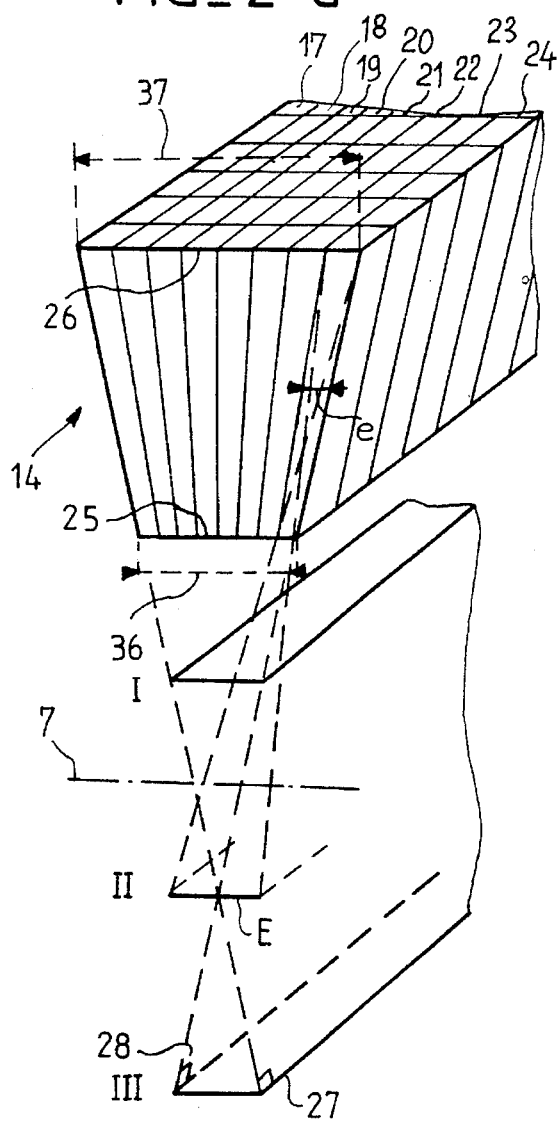
FIG_2-a
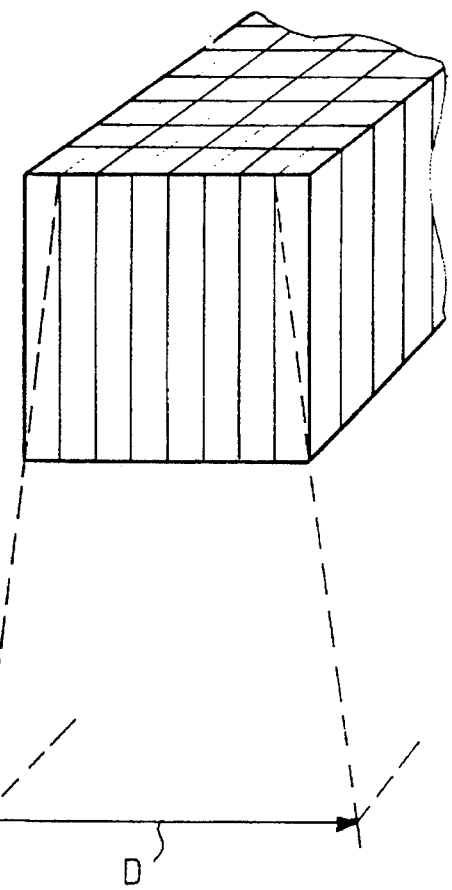
FIG_2-b
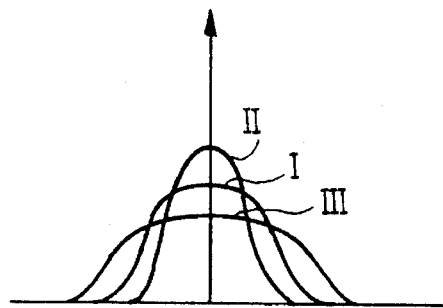
FIG_3-a
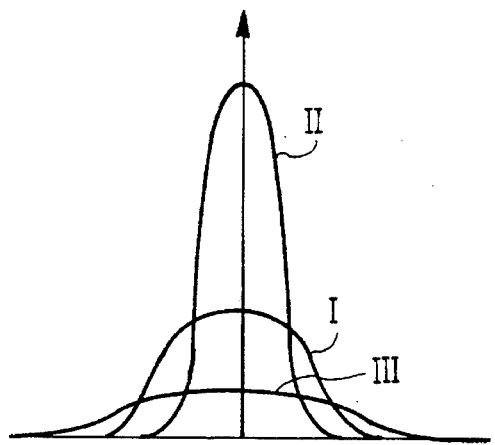
FIG_3-b

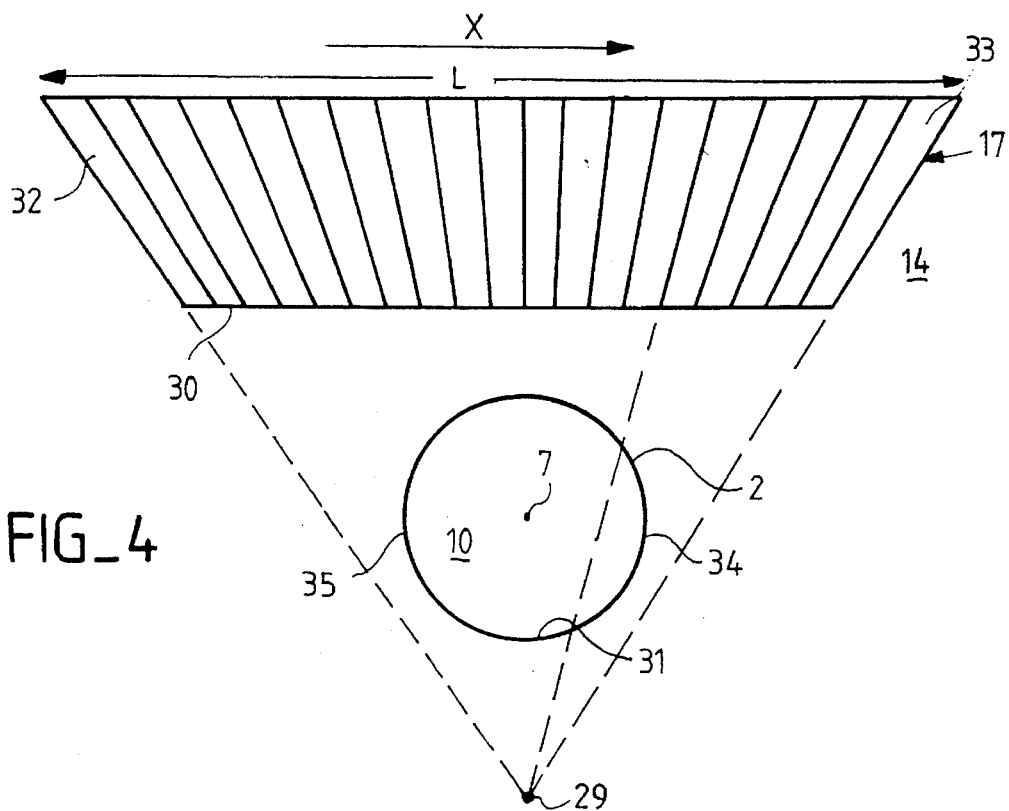
FIG_4
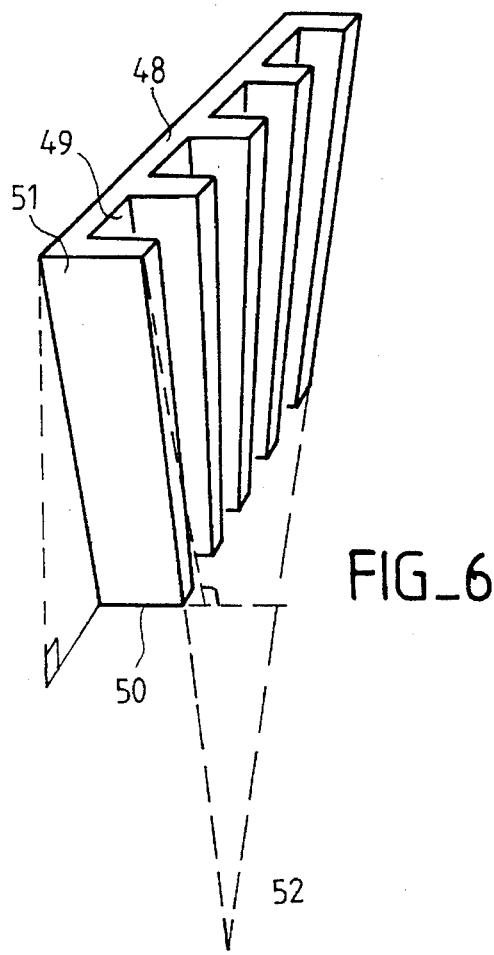
FIG_6
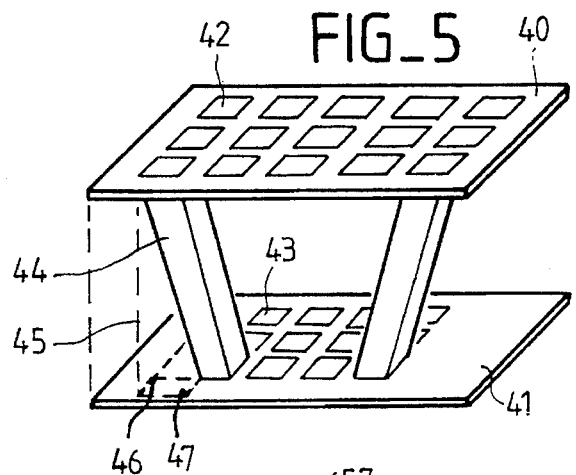
FIG_5
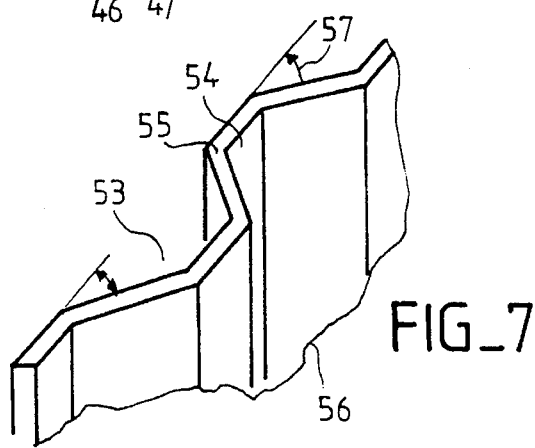
FIG_7

TOMOGRAPHY MACHINE WITH GAMMA-RAY DETECTION

This application is a continuation of U.S. patent application Ser. No. 07/920,314, filed Oct. 23, 1992.

FIELD OF THE INVENTION

The field of the present invention is an improved tomography machine with gamma-ray detection. It can be applied more particularly in the field of nuclear medicine but can also be used in industrial controls. It is aimed at improving the performance characteristics, in terms of spatial resolution and sensitivity, of gamma-ray tomography machines of the prior art. The tomography referred to herein is the reconstructed type of emission tomography, identical to the one known in the field of X-ray tomodensitometers.

BACKGROUND OF THE INVENTION

Reconstructed type tomography is used to present images of sections of a body. These images of sections are reconstructed from image projections obtained while a detector rotates about an axis passing through a body to be studied, perpendicular to the image sections to be produced. In the X-ray field, the image projection is generally a line image projection: the detector comprises a row of aligned detectors, facing the X-ray tube, in the plane of the section. In recent developments, however, the image projection is a 2D image projection: the detector has a plurality of detector cells arranged in two axes perpendicular to the main axis of X-ray emission.

In the field of nuclear medicine, the image projections are initially 2D images. These 2D image projections are related to the structure of the gamma cameras used in the tomography machines. A gamma camera is used in nuclear medicine for the display, in an organ, of the distribution of molecules marked by a radio-active isotope injected into a patient. Thus, a gamma camera has a collimator to focus the gamma photons emitted by the patient's body, a scintillator crystal to convert the gamma photons into light photons or scintillations, and an array of photomultiplier tubes, each of which converts the scintillations into electrical pulses. The scintillator and the collimator are normally constituted by flat plates: the image projections along a main orientation of the scintillator, perpendicular to its plane, are 2D images. A gamma camera further comprises electronic circuits for the production, from the electrical signals given by the tubes, of signals of coordinates X and Y of positions on the scintillator at which the scintillations are produced. A detection system such as this is followed by a processing and display unit that can be used to obtain an image projection of the distribution of the radioactive isotopes in the patient during the acquisition of the image.

Among other qualities, a gamma camera should possess high spatial resolution, namely the capacity to distinguish between small radioactive sources that are close to one another, and good response in terms of counting rate, namely the capacity to process a large number of gamma photons per unit of time. The spatial resolution depends on the accuracy of computation of the coordinates X and Y. The quality of the preparation of these coordinates depends essentially on physical laws that govern the working of the different parts of the gamma camera. Thus, the interaction of a gamma photon with the crystal gives rise to a light scintillation, the intensity of which decreases exponentially with time. The time constant of this decrease is characteristic of the scintillator crystal used. For a thallium-activated sodium iodide NaI(Tl) crystal, it is of the order of 250 nanoseconds.

A scintillation is seen by several photomultiplier tubes simultaneously. The light photons forming this scintillation liberate photoelectrons from the photocathodes of the photomultiplier tubes. For a scintillation with a given energy level, the number of photoelectrons thus liberated is governed by a Poisson statistical law. This means that the electrical signal delivered by a photomultiplier tube receiving a scintillation has an amplitude, the value of which follows a Posson statistical distribution and the mean value of which is a function of the energy of the incident light photons.

It can thus be assumed that a gamma ray gives rise, in a scintillator, to about ten thousand photons. The efficiency of the photomultiplier tubes is generally low, about ten per cent. The result thereof is that for a given scintillation, only several hundreds of light photons (for example 700) are detected by the photomultiplier tube. However, for these detected photons, the electrical signal delivered by the photomultiplier tube fluctuates according to the Poisson law referred to. This fluctuation is due to the mode of detection by the tubes: it relates to the liberation of electrons from the dynodes of the tubes. Owing to the quantum character of this liberation and the small number of effective instances of liberation, it is necessary to take account of the statistical phenomenon.

A scintillation is normally omnidirectional. The scintillator in itself absorbs a part of the energy from the scintillations before delivering the light photons in such a way that, as and when the distance from the place where the scintillation is produced increases, the light energy emitted by the scintillator decreases exponentially. This has two consequences: firstly, a scintillation will excite several photomultiplier tubes in this way. Secondly, this exponential decrease itself will be turned to advantage to enable the recomputation, from all the signals given by all the photomultipliers, of the place in which the scintillation is produced. A computation such as this is described, for example, in the French patent application No. 83 08825 filed on 27th May 1983. The image projections thus acquired commonly have a resolution of the order of 5 mm. This means that it is possible, with images such as these, to differentiate in the image between two objects at a distance of less than 5 mm from each other, or objects larger than 5 mm.

To carry out operations of tomography, it is necessary to acquire a number of these 2D image projections, while a main direction of examination of the gamma camera takes different orientations with respect to the body. These different orientations are obtained by mounting the gamma camera on a mount capable of making it rotate about an axis passing through the body perpendicularly to the sections to be produced.

The collimators used in the gamma cameras are regarded as a thick, flat plate made of a material that is opaque to the gamma rays in which elongated holes, all parallel to one another, are made. These holes are oriented perpendicularly to the planes of the collimator and of the scintillator. They make it possible to prevent the effects of scattering of the gamma rays, as well as to eliminate those gamma rays which would not propagate perpendicularly to the plane of the scintillator. Consequently, the scintillations occur normally in the scintillator in a position, in straight forward projection, vertical to the place where the gamma emissions have occurred in the body.

The implementation of the known algorithms for the reconstruction of tomographic images then makes it necessary to convert the 2D image projections thus acquired into line image projections. If it is assumed that the axis of rotation of the gamma camera is parallel to Y and if the 2D image projections possess pixels aligned parallel to Y, on the one hand, and parallel to X (perpendicular to Y) on the other hand, it is necessary, in order to acquire a line image, to take account only of those elements of the image projection which are located in an image band parallel to X. This band should always be chosen at the same place in the different image projections concerned. These line images enable the reconstruction of the image of an examined slice. This slice is, during the examination, vertically facing these bands.

According to a method such as this, it is possible theoretically to reconstruct as many sectional images in the body as there are bands likely to be made in the image projections. Thus, if an image projection is divided into 20 bands, and if, each time, the processing operations are made on corresponding bands, it is possible to obtain 20 sectional images. For an examined field of the order of 20 cm, images of slices are thus obtained with a thickness equal to 1 cm.

However, this is only the theoretical result. In practice, it can be shown that the real width of the slice taken into account by a band, with an electronic type of selection such as this, is widening from one side, the thickness of which is equal to the width of the band, up to the other side. The increase in the thickness of the slice varies with the width of the holes and varies inversely proportionally to the length of the holes. Furthermore, it can be shown that the sensitivity of detection varies enormously depending on whether the place from which the gamma emission emanates in the slice is close to the rotational axis of the gamma camera or is at a distance from it. The approach that would consist in reducing the dimensions of the holes comes up against the problem of an excessive drop in sensitivity: the solid angle that illuminates an elementary surface of the scintillator gets reduced, in effect, as the square of the reduction of the holes. Given the omnidirectional nature of the gamma rays emitted, the number of the gamma rays detected would be reduced correspondingly, which would diminish the efficiency of the gamma camera.

BRIEF DESCRIPTION OF THE INVENTION

In the invention, it has thus been possible to determine that the sensitivity of detection with respect to a unit volume element of the object to be reconstructed (this sensitivity being expressed by the number of information elements received per second and per cm3 of this object, for a given level of radioactivity) leads to modifying the shape of the collimator. In so doing, it has then been realized, in the invention, that this modification of the collimator makes it possible furthermore to obtain a minimum variation of this sensitivity as a function of the depth of detection in the slice. This makes it possible to provide for a precise modelling of the detector in the reconstruction algorithm.

In the prior art, to increase the sensitivity of detection while at the same time preserving an acceptable level of spatial resolution, it was possible to resort to increasing the number of gamma cameras rotating about the patient. This approach has the following disadvantages among others. It does not increase the sensitivity in the direction of projection corresponding to a given orientation. It makes it possible only to go faster at the instant of the acquisition, given that several projections are acquired simultaneously, in several different directions. In another approach, described in a European patent application No. 84 110348.4, one or more rings of detectors have been proposed. These approaches have the drawback wherein the field of examination is small. In practice, it is reduced in such a way that only the human brain can be examined. Furthermore, the collimators cannot be changed to enable the examination of gamma radiation with an energy of over 200 Kev.

The document U.S. Pat. No. 3,509,341 teaches the use of a focused collimator in nuclear medicine. However, this document does not concern tomography and, furthermore, the focal point of the collimator is placed in the patient. The document DE-A-2 351 450 takes up the same elements. The document FR-A-2 471 610, apart from the fact that it does not even come within the field of nuclear medicine, relates only to so-called transmission tomography, with an X-radiation that goes through the patient, while the invention relates to emission tomography in which the focus of emission of the gamma rays is in the body. As shall be seen, the invention shows that there is an improvement of the resolution of the images produced in relation to these teachings, when the focal point of the collimator is fixed beyond the patient's body, while the focus of emission of the gamma rays is in the patient's body.

It is an object of the invention to overcome these drawbacks by making an a priori choice of the thickness of the slice in which it is sought to make the image. The thickness of the section, then, is not the result of an a posteriori deduction of the localization and of the thickness of the bands used in the image projections. In the invention, the detection is focused on the emissions of the gamma rays that occur in these slices. This focusing furthermore has an effect of magnification because, on the photomultiplier tubes side, it involves a width of the scintillator that is greater than the thickness of the slice examined. This is obtained by a convergent focusing of the collimator towards the concerned slice. In so doing, firstly an increase is achieved in the sensitivity and, secondly, it can be seen that this sensitivity is then substantially the same throughout the slice, regardless of the depth in the body at which the concerned gamma emissions occur. To simplify the description, in the invention, the width of the "detector band" assigned to the thickness of a slice is greater than this slice thickness.

It is thus possible to acquire line image projections relating to several slices simultaneously. Subsequently, the gamma camera is shifted longitudinally, and the total operation of acquisition is reiterated for slices interleaved with the already acquired first slices. It will be shown that, despite this repetition, the making of a set of adjoining tomographies is faster than in the prior art, given the gain in sensitivity of the gamma camera.

An object of the invention therefore is a gamma ray detection tomography machine comprising:

a patient-bearing bench to support a patient to be examined, a gamma camera and a mount bearing this gamma camera, this mount comprising means to make the gamma camera rotate about an axis going through the patient's body, and means to acquire image projections of the body for different orientations of the mount, holes having a base, close to the body, and a summit, close to the scintillator, the surface of the section of the base of a hole being smaller than that of its summit, the midpoints of the bases of two neighboring holes, in any two neighboring series in an arrangement, being closer to each other than the midpoints of the summits of these holes, the holes each possessing a main direction going through the midpoints of their base and of their summit, and in that, a main direction of the holes of a same series is contained in a focal plane, this focal plane defining, with the other focal planes of the other series of a same arrangement, a tomography slice relative to this arrangement.

The invention will be understood more clearly from the reading of the following description and from the examination of the figures that accompany it; these figures are given purely by way of an indication and in no way restrict the invention. Of these figures:

BRIEF DESCRIPTION OF THE FIGURES

FIG. 1 is a general schematic drawing of a tomography machine according to the invention;

FIGS. 2a and 2b are comparative drawings of the structure of a collimator according to the invention and according to the prior art respectively;

FIGS. 3a and 3b are comparative drawings of the statistics of detection relating to the invention and according to the prior art respectively;

FIG. 4 shows an improvement of the collimators of the invention;

FIGS. 5, 6 and 7 show exemplary embodiments of the collimators according to the invention.

DETAILED DESCRIPTION OF THE INVENTION

FIG. 1 shows a tomography machine according to the invention. This tomography machine has a patient-bearing bench 1 to bear a patient represented schematically by a cylinder 2. The tomography machine comprises a gamma camera 3 and a mount 4 borne by a pedestal 5. The mount can rotate along the arrow 6 about an axis 7 passing substantially through the middle of the patient's body 2. In one improvement, to accelerate the acquisition, the mount may have a second gamma camera 8 identical to the first gamma camera 3 and located symmetrically to said camera 3 in relation to the axis 7. There are other possible embodiments that restrict neither the field examined nor the possibilities of access to the patient. The gamma camera 3 may furthermore be brought closer to the body 2 or moved away from it by a spacing mechanism 9. This spacing mechanism is such that, even if there is only one gamma camera 3, the mount is always balanced in rotation with respect to the axis 7.

The gamma camera comprises means to acquire image projections of the body while it takes up different orientations with respect to this body. These means of acquisition comprise, on the path of the gamma rays emitted from a slice such as 10 in the patient, a collimation device 11, a scintillator unit 12 and an array 13 of photomultiplier tubes. The tubes deliver electrical signals corresponding to scintillations produced by the scintillator 12, in reaction to excitations by gamma photons. The electrical signals are processed in electronic circuits 62 to produce image projections of the slices 10 of the patient's body. The processing referred to in these circuits 62 is, for example, of the type described in the French patent application referred to here above.

What characterizes the invention is the particular feature of the focusing of the holes of the collimator of the invention. This focusing is symbolized, in FIG. 1, by the trapezoidal character of the arrangements of holes of the collimator 11. In this figure, three arrangements of holes have been shown, placed side by side and numbered 14 to 16. In practice, a tomography machine may comprise five or even more of these arrangements. In a preferred example, each arrangement has eight series of holes. To avoid excessively burdening the drawing of FIG. 1, the arrangement 14 is shown with only four series of holes. By contrast, FIG. 2 shows that the arrangement 14 has eight series of holes referenced 17 to 24. The holes have a base, for example the base 25, close to the body. They also have a corresponding summit 26, close to the scintillator. The area of the section of the base of a hole is smaller than that of its summit. This means that the holes widen out from their base onwards. A hole has a main direction going through the midpoints of its base and its summit.

Furthermore, the midpoints of the bases of two neighboring holes, in any two neighboring series, for example the series 20 and 21, of a same arrangement, are closer to each other than the midpoints of the summits of these holes. This means, furthermore, that the main directions of neighboring holes belonging to two distinct neighboring series will go on approaching each other in the direction of the body. Finally, the main directions of the holes of a same series are contained in a same plane corresponding to this series. The different planes of the series belonging to a same arrangement go through the body and together demarcate the thickness of the slice.

A schematic view has thus been given in FIG. 2a of the focal plane 27 corresponding to the series of holes 17 and the focal plane 28 corresponding to the series of holes 24. These two planes demarcate, in the body (not shown), a slice of the profile thereof having the shape of a flared-out hat. It can be shown that, given the aperture 14 of the holes, the slice thus selected has a minimum thickness located in the middle and determined, firstly, by the value of E and, secondly, by the distance of this midpoint from the collimator. The thickness E of the slice at the middle of the flared-out hat is then little different from, for example half of, the thickness of the slice on each side of this middle.

On the contrary, as FIG. 2b shows, under the same conditions with a prior art collimator having parallel holes, and with holes of comparable dimensions, it is seen that the thickness at mid-height of the selected slice corresponds to the emissions of gamma rays that arise in a width D, without any comparison to what happens in the small width E according to the invention. Furthermore, the number of the gamma emissions detected is equally great in both cases. However since, in the invention, the emissions come only from one slice, the sensitivity relative to this slice is increased. Consequently, the a priori determination, in the invention, of the thickness of the slice is quite advantageous as compared with an a posteriori selection, with the selection of bands in 2D image projections obtained by the gamma camera provided with a standard collimator having parallel holes.

The advantage of the invention is obtained because all the focal planes of the series 17 to 24 intersect substantially along the rotational axis 7. Furthermore, in regions I, II, III, located at different depths in the body, the statistical law of detection varies little whereas it varies enormously in the prior art. Indeed, as FIGS. 3a and 3b show, the sensitivity of detection for the regions I, II and III is substantially constant with the invention, while it undergoes a very great increase for the central region II in the prior art. This greater sensitivity is quite simply related to the thickness taken into account which is greater for a same band in each image projection.

FIG. 4 shows another particular feature of the collimator according to the invention. Indeed, along the direction X (perpendicular to the direction Y which is parallel to the axis 7 : see FIG. 1), the collimation holes of a series are furthemore focused, in the focal plane of their series, towards a focal point 29. FIG. 4 thus gives a view, above the body 2, in the arrangement 14, of the holes 17. Preferably, the focal point 29 is a greater distance from the lower plane 30 of the collimator 11 than the midpoint 7 of the body 2 or even than that part 31 of this body which is at the greatest distance from the collimator 11. In one example where an arrangement of collimations has a length L substantially equal to 56 cm, the distance between the plane 30 and the focal point 29 is of the same order of magnitude as L. It can easily be shown that, here again, a very major gain in sensitivity is obtained because all the holes of the collimator see the body 2, regardless of the orientation of the mount 4.

In practice, the focal point 29 is chosen at a distance such that the farthest holes 32, 33 of the series 17 in the arrangement 14 see the lateral edges 34 and 35 respectively of the body 2. It can be shown that the phenomenon of magnification thus prompted, firstly by the intersection of the planes along the axis 7 and secondly by the main directions of the holes of a series intersecting each other, at a point 29, leads to an improvement of the sensitivity which enables the camera to achieve far swifter acquisition of a line image projection, for example that of the slice 10.

In one exemplary embodiment, the width 36 of the base of an arrangement of holes is of the order of 4 cm, and the width 37 of the summit of this arrangement is of the order of 6 cm: i.e. it is of the same order of magnitude as that of the known space requirement of the photomultiplier tubes. In this example, the width or effective thickness of the slices is of the order of 1.3 cm. In other words, for a space requirement of 6 cm, the image of a 1.3 cm slice is obtained. In FIG. 1, it is noted that the arrangements 14, 15, 16 and those that follow are contiguous so that the slices 10, 38, 39 and those that follow, which are respectively seen by each of these arrangements, are at a distance of about 6 cm. from one another. The slices 10, 38, 39 etc. are not contiguous. If the explored sections are to be contiguous or adjoining, the gamma camera 3 (or the gamma cameras 3 and 8) should be shifted in the direction Y, by a length equal to the width of an acquired slice. It is observed then that, in five successive shifts, it is possible to build five groups of tomographic images interleaved with each other: 5× 1.2 cm=6 cm.

In view of the greater sensitivity obtained with the scintilator of the invention, it has been possible to limit the period of acquisition of all the image projections to about six minutes for an activity, at the center of the body, of 100 pulses/µCi/cm3. In six minutes, for each of the arrangements 14, 15 or 16 and those that follow, there are thus carried out 64 line projections along 64 different orientations of the mount about the body 2. The period of acquisition, for each projection, is of the order of five seconds if both gamma cameras 3 and 8 are used. At the end of six minutes, the camera 3 is shifted in the direction Y by a step equal to the thickness of a slice. The operation is thus repeated five times in succession. Ultimately, at the end of 30 minutes, the necessary projections are acquired to reconstruct 5×N tomographic images in the body 2. N is the number of arrangements of series of holes of the collimator 11.

FIGS. 5, 6 and 7 show different ways of making arrangements of holes of the collimators according to the invention.

In the first example, represented by FIG. 5, two copper plates 40 and 41 are used, each pierced with as many holes as the arrangements should contain. These holes such as 42 and 43, respectively in the plates 40 and 41, are positioned in these plates at the place that should be occupied by the orifices of these holes in the collimator once it is made. The holes 42 in the plate 40 are larger than and not as close to each other as the holes 43 in the plate 41. Furthermore, square-sectioned conical needles 44 are made, the tips of which are finer and are engaged in the holes 43 and the bases of which are larger and are engaged in the holes 42. In FIG. 5, an upright vertical line 45 and horizontal reference axis 46, 47 show the focusing character of the arrangement of the needles 44 between the two plates 41 and 40. Once all the needles 34 have been positioned between the holes 42 and 43 of the plates, the assembly is slipped into a mold and molten lead is cast so that the lead occupies the place left free between the needles. After cooling, the mold is stripped and the needles are driven towards the biggest holes 42.

FIG. 6 shows another simpler exemplary embodiment. This embodiment uses a thick lead plate 48 in which grooves such as 49 have been cut. The plate 48 has the particular feature of not being plane but of comprising, on the contrary, one edge 50 which is less thick than an opposite edge 51. The edge 50 is designed to be placed close to the body, the plate being made to stand on edge. The edge 50 is taken to be less thick than the edge 51 only insofar as it is sought to obtain the focusing at the point 29 (FIG. 4). The grooves 49 are made from one edge to the other, on the same face of the plate 48, in such a way that each of them has a mean direction tending to converge at a common point 52. This common point 52 belongs to a straight point intersecting the axis 7 when the plates are in position in the arrangement of corresponding holes of the collimator.

To constitute an arrangement such as this, as many of these grooved sheets are stacked on one another as there are holes in a series of holes of the arrangement. In the preferred exemplary embodiment, in which the length L of an arrangement is of the order of 50 cm, about fifty grooved plates are thus stacked against one another so as to produce about fifty holes in each series. Normally, the sheet has as many grooves 49 as there are series in the arrangement. Only four of them have been shown herein, in order to simplify the drawing.

FIG. 7 shows a third exemplary embodiment of the arrangements of the collimator according to the invention. Rather than using the grooved sheets, this embodiment uses sheets folded so that they constitute semi-housings 53 and 54, positioned on either side of the sheet, one behind the other in the sequence forming the sheet, in the manner of a corrugated sheet. The housings 53 and 54, like the grooves of the sheet 48, keep decreasing in thickness and, furthermore, get transversally ever finer with distance from the edge 55 which is designed to be placed close to the scintilator in the direction of the opposite edge 56 of the sheet that is designed to be placed close to the body. To constitute the series of holes, half-housings of two successive sheets, offset in alignment from one housing to another, are attached against one another. They form a honeycombed network that can be likened to the arrangements of series of holes seen here above. In the present case, from one series to another, the holes are offset in front or in the rear by a half-step. There are as many folded sheets according to FIG. 7 as there are holes plus one in a series of holes. It can be shown that by choosing an angle of fold as close as possible to 90°, and by tolerating rounded features at the fold with a radius of 0.5 mm, it is easy to meet the constraints of septal absorption of the gamma rays in the thickness of the sheet.

It is possible, according to the invention, to use holes that are oriented in parallel to one another in each series of holes or else oriented towards the focal point 29. As the case may be, use will be made respectively of an algorithm for the reconstruction of tomography images, which is a parallel beam algorithm, or a reconstruction algorithm for fan beams. This algorithm is implemented by known type processing means 70. It is seen that the choice of the point 29, distant from the furthest end 31 of the body 2, makes it possible to choose reconstruction algorithms already used in third-generation X-ray tomodensitometry (so-called fan beam reconstruction algorithms). The latter procedure contributes to greater sensitivity of the gamma camera.

To make the scintillator element 12, FIG. 1, preference will be given to using scintillator crystal bars such as 58 positioned exactly vertically to an arrangement of holes. The thickness of these bars is chosen according to known criteria. A light conduit 59 is positioned between the scintillator bars 58 and the array 13 of photomultiplier tubes. The light conduit 59, preferably made of glass, takes the form of a glass slab that covers all the rods such as 58. To prevent the scintillations emitted by a bar 58 from exciting the photocathodes of the photomultiplier tubes positioned vertically to another neighboring arrangement (arrangement 15), grooves such as 60, oriented in parallel to the arrangements and between the different arrangements, are made in the light conduit 59. In FIG. 1, the grooves have a triangular profile. Their base is oriented towards the scintillator, and their vertex is positioned on the photomultiplier tube array 13 side. The grooves 60 are, however, not so deep as to break the light conduit 59.

The first advantage of this is that it enables the making of a light conduit formed by a single piece, in a relatively simple way. The second advantage of this approach is that it avoids the losses of light photons that result from scintillations in a bar 58 of the scintillator and get propagated in a direction parallel to the direction Y to excite the tubes located vertically to a neighboring arrangement. Preferably, the grooves 60 are even filled with magnesium oxide which, with its white color, has the effect of achieving maximum reflection of the photons of light scattered towards the photomultiplier tubes which they must excite. In this way, a relatively simple separation is achieved of the gamma emissions coming from the slices studied and going to the rows 61 of the photomultiplier tubes located vertically to the scintillator bars 58. Furthermore, the reflected gamma photons then contribute, by barycentration, to the localization in the direction X. There is then no loss of sensitivity.

The photomultiplier tubes of the array 13 are arranged in such a way that a row of tubes is positioned vertically to each bar. If the tubes are square-sectioned, the alignment raises no difficulty. If the tubes are hexagon-sectioned, the width of the bar is equal to the side of the hexagon.

The first consequence of this method is that it simplifies the computations of barycentration of the place at which a scintillation has occurred in the scintillator. Indeed, as the processing circuit 62 shows, it is necessary, along the axis X, to look for the abscissa of the place where a scintillation has occurred. The ordinate is automatically acquired as being that of a concerned row of tubes 61. In other words, in carrying out solely the barycentration $$(x+-x-) / (x++x-)$$

it is possible directly to obtain a line image projection 63, relative to the examination of the slice 10, for a given orientation of the mount 4 with respect to the body 2.

The second consequence is that all the scintillations which, normally, with a standard collimator, would excite tubes corresponding to adjacent slices, are now taken into account by the concerned row of tubes.

It has furthermore been shown, in FIG. 1, that the standard use of gamma cameras, with parallel hole collimators, was aimed at acquiring 2D image projections (such as 63 to 65) corresponding to different orientations of the gamma camera about the body 2. With these images 63 to 65, the reconstruction in volume was done by the selection, each time, in each of these images, of the bands of images 66 to 68 respectively. In view of the advantages thus indicated, in the invention, the alignment of photomultiplier tubes 61 are preferably arranged directly vertically and parallel to the direction X of the bars 58.

We claim:

1. In a gamma ray detection tomography machine including a bench for supporting a patient being examined, a gamma camera receiving gamma rays emitted by the patient and comprising:

means rotationally mounting the camera about an axis passing through the patient; means for collimating gamma rays emitted from the patient and including an array of elongated adjacent apertures formed through a thickness of material opaque to the gamma rays,
   (a) the array of apertures being divided into arrangements of apertures, the arrangements of apertures focusing gamma rays coming from individualized tomographic slices in the patient, the apertures having a base confronting the patient, and a top confronting an aligned scintillator, the tomographic slices being perpendicular to the axis;
   (b) the area of each aperture base being smaller than the area of each aperture top;
   (c) the centers between two adjacent aperture bases being closer than the centers between corresponding aperture tops;
   (d) the centers of each aperture top and corresponding base defining a main direction line;
      (i) all of the respective main direction lines, associated with a rectilinear series of adjacent apertures within an arrangement, being located in the same focal plane, adjacent focal planes relative to an arrangement defining a tomographic slice perpendicular to the axis by intersecting each other within the slice in the patient corresponding to the arrangement, the main direction lines of the apertures in each series intersecting behind the body;
      (ii) all of the main direction lines, associated with a linear series of adjacent apertures, intersecting at a unique focal point;
   an array of photomultiplier tubes located in aligned spaced relation with the scintillator for generating signals representing tomographic slice images taken perpendicular to the patient axis; and
   circuit means for processing signals derived from the tubes and producing reconstructed tomographic images therefrom.

2. A tomography machine according to claim 1, wherein the main direction lines associated with a given linear series of adjacent apertures intersect at a focal point in a corresponding focal plane, and wherein the distance of this focal point from the scintillator is greater than the distance between the scintillator and the patient axis.

3. A tomography machine according to claim 2, wherein the focal point of a particular focal plane is located at a distance from the scintillator which is substantially equal to the length of the scintillator, measured in a direction of a corresponding linear series.

4. The tomography machine according to claim 1, wherein the scintillator further comprises:
- a set of scintillator bars having a first surface thereof positioned in aligned parallel spaced relationship with the aperture array, an opposite surface of the scintillator bars located in parallel aligned and spaced relationship with a light conduit and further having
  (a) a single plate made of material transparent to light rays emitted by the scintillator; and
  (b) the plate being provided with grooves oriented parallel to a first direction of the aperture array.

5. A tomography machine according to claim 4, wherein the grooves of the light conduit are filled with magnesium oxide.

6. A tomography machine according to claim 1, wherein:
- the array of photomultiplier tubes is arranged along orthogonal axes, at least one of these axes being perpendicular to axis of the tomography machine;
- the tubes are aligned, in registry width correspondingly positioned apertures, along the alignment axis of the tubes; and
- the circuit means include means for producing a line image projection of the gamma ray emissions emitted from a tomographical slice.

7. The tomography machine according to claim 1, wherein the aperture array is fabricated from lead.

8. The tomography machine according to claim 1, wherein the aperture array is fabricated in the form of corrugated sheets.

9. The tomography machine according to claim 1, wherein the aperture array is fabricated from an assembly of grooved sheets.

10. The tomography machine according to claim 1, together with means for translating the mounted camera along a direction parallel to the patient axis for producing axially spaced tomographic slices along a direction parallel to the patient axis.

* * * * *